(12) United States Patent
Diebold et al.

(10) Patent No.: US 8,854,060 B2
(45) Date of Patent: Oct. 7, 2014

(54) PHYSIOLOGICAL MEASUREMENT INSTRUMENT

(75) Inventors: Michael Diebold, Kilchberg (CH); Jens Philipp, Berlin (DE); Thomas Finnberg, Wallisellen (CH)

(73) Assignee: BIOTRONIK CRIM Patent AG (CH)

( * ) Notice: Subject to any disclaimer, the term of this patent is extended or adjusted under 35 U.S.C. 154(b) by 628 days.

(21) Appl. No.: 12/917,183

(22) Filed: Nov. 1, 2010

(65) Prior Publication Data

US 2011/0109329 A1 May 12, 2011

Related U.S. Application Data

(60) Provisional application No. 61/258,622, filed on Nov. 6, 2009.

(51) Int. Cl.
| | |
|---|---|
| *G01R 27/26* | (2006.01) |
| *A61B 5/00* | (2006.01) |
| *G01B 11/02* | (2006.01) |
| *G01B 7/02* | (2006.01) |
| *G01B 11/00* | (2006.01) |
| *A61B 5/0205* | (2006.01) |
| *G01K 13/00* | (2006.01) |
| *G01B 21/04* | (2006.01) |
| *G01K 1/02* | (2006.01) |
| *A61B 5/024* | (2006.01) |
| *A61B 5/1455* | (2006.01) |
| *A61B 5/021* | (2006.01) |

(52) U.S. Cl.
CPC ............ *G01R 27/2605* (2013.01); *A61B 5/024* (2013.01); *A61B 5/681* (2013.01); *A61B 5/14551* (2013.01); *A61B 5/0022* (2013.01); *G01B 11/026* (2013.01); *A61B 5/021* (2013.01); *G01B 7/023* (2013.01); *A61B 2562/0257* (2013.01); *A61B 2560/0456* (2013.01); *G01B 11/002* (2013.01); *A61B 5/02055* (2013.01); *A61B 2560/0462* (2013.01); *G01K 13/002* (2013.01); *A61B 2560/0468* (2013.01); *G01B 21/04* (2013.01); *G01K 1/02* (2013.01)

USPC ........... 324/679; 324/663; 324/658; 600/300; 600/310

(58) Field of Classification Search
CPC ...... G01R 27/2605; G01D 5/24; A61B 5/024; A61B 5/0205; A61B 5/681
USPC ........... 324/679, 658; 356/614; 374/E13.001, 374/185; 600/300–301, 309–310, 347, 600/322–326, 354–365, 509, 513, 547, 600/549; 128/905, 920; 340/539.12, 573.1; 333/124

See application file for complete search history.

(56) References Cited

U.S. PATENT DOCUMENTS

| | | | |
|---|---|---|---|
| 6,762,685 B2 * | 7/2004 | Muto et al. | 340/573.1 |
| 7,052,472 B1 * | 5/2006 | Miller et al. | 600/549 |
| 7,285,090 B2 * | 10/2007 | Stivoric et al. | 600/300 |

(Continued)

*Primary Examiner* — Amy He
(74) *Attorney, Agent, or Firm* — Craig A. Fieschko, Esq.; DeWitt Ross & Stevens S.C.

(57) ABSTRACT

A physiological measurement instrument is disclosed, having a detector, implemented as one or more sensors, for measuring values of one or more physiological measured parameters associated with a body of a human or animal subject, and for detecting values of a physical parameter that indicates an operating position of the measurement instrument relative to the body, and an operating-position-determining unit that receives and analyzes output signals from the detector, to determine the operating position of the measurement instrument.

28 Claims, 12 Drawing Sheets

(56) References Cited

U.S. PATENT DOCUMENTS

| | | |
|---|---|---|
| 7,367,949 B2 * | 5/2008 | Korhonen et al. ............ 600/483 |
| 7,502,643 B2 * | 3/2009 | Farringdon et al. ........... 600/509 |
| 7,526,327 B2 * | 4/2009 | Blondeau et al. ............. 600/310 |
| 7,911,345 B2 * | 3/2011 | Potyrailo et al. ........... 340/572.1 |
| 2008/0214949 A1 * | 9/2008 | Stivoric et al. ................ 600/549 |
| 2009/0128441 A1 * | 5/2009 | Sangawa ....................... 343/860 |
| 2009/0278685 A1 * | 11/2009 | Potyrailo et al. ........... 340/572.1 |
| 2010/0013572 A1 * | 1/2010 | Shannon et al. .............. 333/124 |

* cited by examiner

PHYSIOLOGICAL MEASUREMENT INSTRUMENT

RELATED APPLICATION

This patent application claims benefit of U.S. Provisional Patent Application No. 61/258,622 filed on Nov. 6, 2009, which is hereby incorporated by reference in its entirety.

TECHNICAL FIELD

The present disclosure relates to a physiological measurement instrument capable of detecting measured values of a physiological measured parameter associated with the body of a human or animal subject.

BACKGROUND

Wearable physiological measurement instruments exist and are used in practice, for example, in the form of wristwatches having a pulse measuring function, blood pressure meters worn on the wrist, or recently in the form of measurement instruments for determining blood oxygen saturation. Measured data for parameters to be monitored are detected by a suitable sensor, saved in the measurement instrument, and optionally processed or transmitted wirelessly to a service center, where they may be combined with other data and may be subjected to a complex analysis for an individual subject, or even for larger groups of subjects as needed, wherein the analytical results may lead to therapeutic measures or statistical conclusions.

It is important when collecting such physiological data from a wearable device, to verify whether or not, at the time of recording the measured values, the measurement instrument was located at its intended site at the body of the test subject (i.e., worn on the body, or, in a more general case, implanted permanently or temporarily within the body). If not, then the data collected may not accurately represent the subject's physiology. Such data would naturally alter the overall monitoring result in an unacceptable manner and would thus affect any statistical conclusions or statements about progress that may be derived therefrom and may even lead to misdirected treatment.

SUMMARY

One objective of the present disclosure is to provide an improved measurement instrument for physiological parameters that avoids these shortcomings. The present disclosure provides and utilizes not only the relevant measured data but also supplementary data indicating an operating position of the measurement instrument in relation to the body of the test subject. Likewise, supplementary data indicating a certain location of the measurement instrument (e.g., on the body, connected to a charging device, or on a table) may also be made available. Thus, relevant measured data is distinguished from irrelevant measured data prior to storage, further processing, or transmission. According to a preferred embodiment, the proposed measurement instrument therefore includes a detector, implemented as one or more sensors, for detecting values of one or more suitable physical parameters that indicate the operating position of the measurement instrument relative to the body or to a certain other location of the measurement instrument. In addition, the proposed measurement instrument has an operating-position-determining unit that receives and analyzes output signals of the detector to determine the operating position of the measurement instrument relative to the body or relative to a certain other location of the measurement instrument.

In a preferred embodiment, a method of detecting absolute values and temporal variation of a position-dependent parameter is formed, and the operating-position-determining unit comprises a comparator for comparing absolute values or time dependent values thus detected against a standard including at least one predetermined threshold value or a comparative parameter. Through suitable adjustment of threshold values, operating positions and non-operating positions of the measurement instrument can be reliably delineated, so that, when it is necessary, several position-dependent parameters may be detected and subjected to a threshold value discrimination, and a decision may be made about the relevance or irrelevance of the measured data thereby detected as a result of combinatorial processing of the position-dependent parameters.

Either data measured for one or more position-dependent physical parameters, or data measured for the same parameter, recorded in different sections of the device, may be subjected to such combinatorial processing. Corresponding embodiments of the measurement instrument thus may include multiple sensors for different physical parameters located in various spatial areas or surface sections of the device, or allocated thereto.

In another embodiment, an operating-position-determining unit produces a binary output signal for characterizing a first operating position at the body as well as a second, additional, remote, operating position, away from the body In yet another embodiment, the operating-position-determining unit may produce a multi-valued output signal for differentiating a first operating position or area at the body, a certain operating position associated with a charging station, and a third, remote operating position away from both the body and the charging station. Thus, in the simpler case, a distinction is made according to whether or not the measurement instrument resides on or in the body in its normal operating position, whereas, according to a more complex data acquisition scheme, two or more different operating positions may be detected and additional differentiated operating-position data may be supplied.

In yet another embodiment, the operating-position-determining unit produces at least one index value, which expresses the probability that the measurement instrument is located in one of several predetermined operating positions, in particular a first operating position at the body or a certain body area, or a second operating position in a charging or docking station, or a third, remote, operating position.

A marker or a binary control signal (on/off) may be used to characterize, delete, block, hold, or forward physiological measured data or, alternatively, to supply a quasi-analog value that can serve as a significance value in processing of the measured data.

According to a preferred embodiment, appropriate for many widely used measurement instruments of the aforementioned type, and simple to implement, the measurement instrument has a two-part or more generally, a multi-part fastener for attaching to the body of a human or animal subject having contact areas provided thereon. When the fastener is closed, the contact areas are in contact with one another; when the fastener is open, the contact areas are not in contact with one another. A detector for the contact status of the fastener contact areas is disclosed.

According to yet another embodiment, the detector has a capacitive sensor system for detecting the proximity of the measurement instrument to the body on a capacitive basis.

According to yet another embodiment, the measurement instrument has at least one radio antenna for emitting a radio signal, and the detector is designed to detect the complex impedance of the antennas. This approach requires few or no structural changes in the measurement instrument, and the sensor system can be implemented as a technical modification of an existing basic circuit design.

According to yet another embodiment, a temperature detector is provided. The temperature sensor is preferably inexpensive and highly reliable. In this embodiment, effective threshold value discrimination is especially important. In particular, both an upper threshold value and a lower threshold value are preferred.

According to yet another embodiment, the detector includes an optical sensor system, deployed in an area of the measurement instrument that faces the body when in use, for optical detection of a neighboring body segment of a charging station. Special measurement equipment, which already includes an optical sensor system for detection of a physical parameter, may enable easily incorporating this optical detection. Furthermore, optically differentiating a skin surface from a plastic surface of a charging station can be implemented reliably, at low cost. In addition, certain specific locations may be differentiated by variations in the data supplied by the optical sensor system.

Yet another embodiment is characterized by a detector, having, in particular, an optical or acoustic sensor system, designed to detect periodic physiological signals, in particular, a pulse rate or heart sounds. This embodiment may be combined with the previous embodiment, above, if an optical sensor system is used.

In yet another embodiment, the detector senses physiological electric potentials, in particular cardiac action potentials or muscle action potentials as a sign of the proximity of a body section to this embodiment, is especially advantageous when the physiological parameter to be monitored is a bioelectric parameter so that parts of the sensor system, and possibly parts of the signal processing system, may be used multiple times.

DESCRIPTION OF THE DRAWINGS

Advantages and expediencies of the present invention are also derived from the following description of exemplary embodiments on the basis of the following figures.

DETAILED DESCRIPTION

Figure 1:
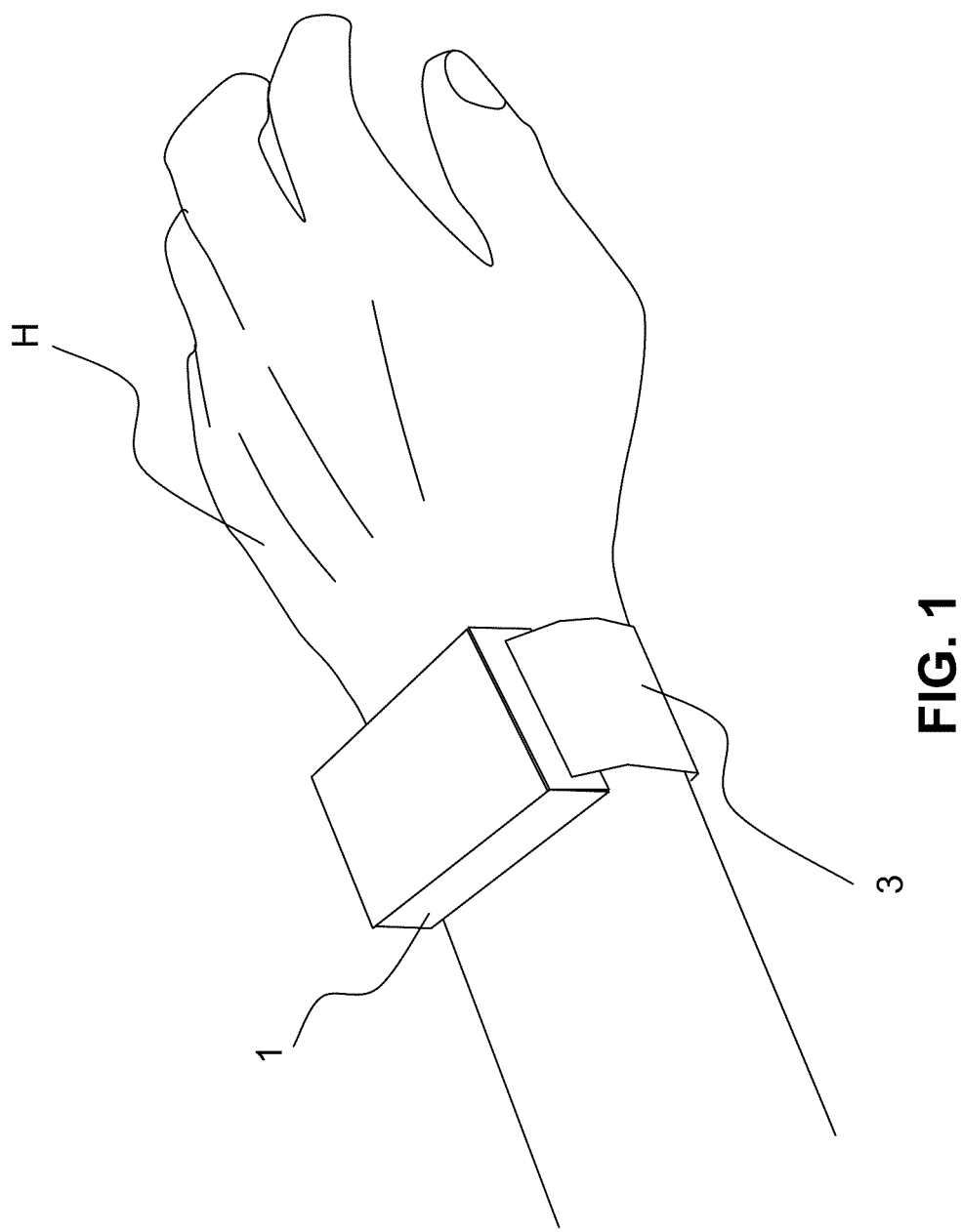
FIG. 1 is a pictorial perspective view of an exemplary wearable measurement instrument.
Figure 2:
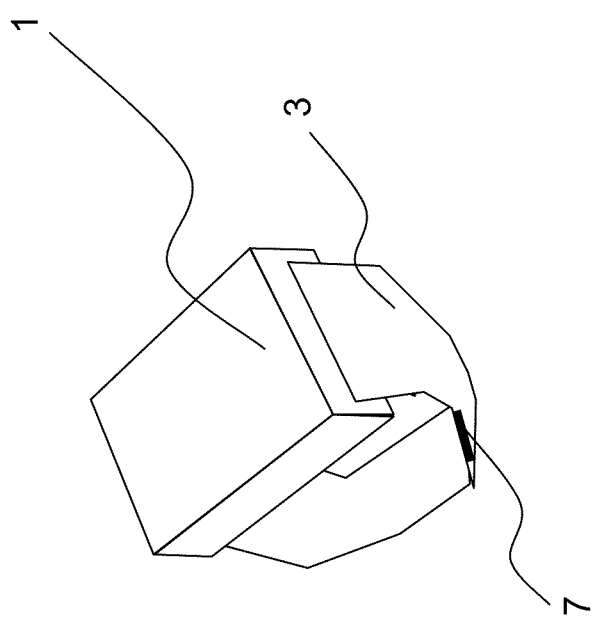
FIG. 2 is a pictorial plan view of the measurement instrument shown in FIG. 1 in which the wristband is closed.
Figure 3:
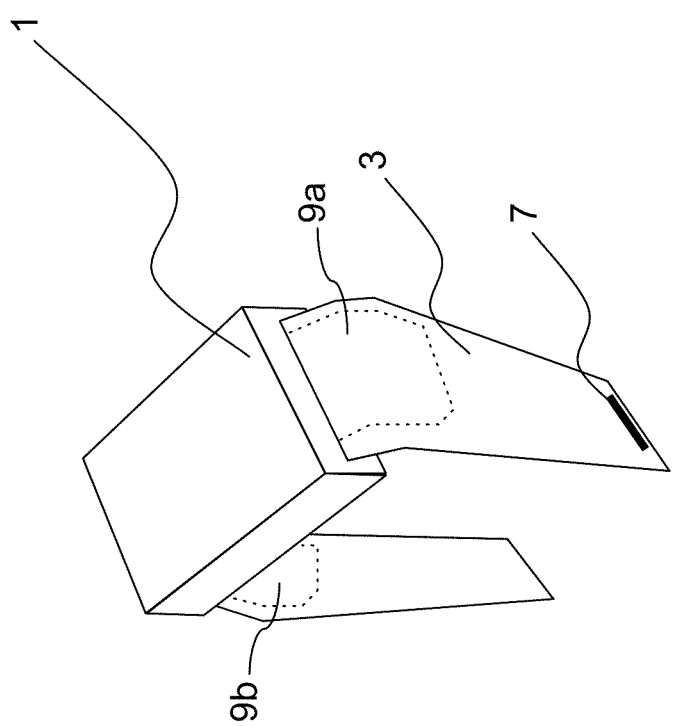
FIG. 3 is a pictorial plan view of the measurement instrument shown in FIGS. 1 and 2 in which the wristband is open.
Figure 4:
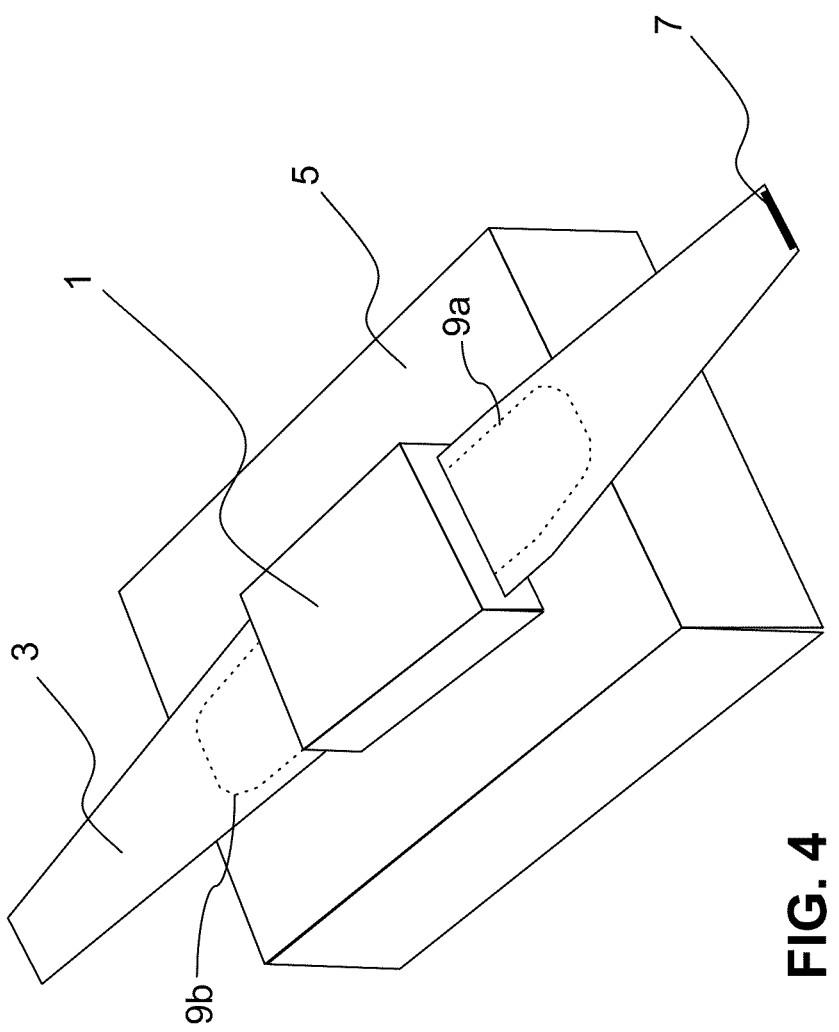
FIG. 4 is a pictorial plan view of the measurement instrument shown in FIGS. 1-3 placed on a charging station.

FIG. 1 shows a wearable measurement instrument 1, which is attached, in the case of a human subject, by a wristband 3 to the wrist of the subject's (i.e., wearer's) hand H and serves to detect physiological measured values of the wearer (e.g., pulse, blood pressure, oxygen saturation, and the like). FIGS. 2, 3 and 4 show, in order, the wearable measurement instrument 1 with the wristband 3 closed, with the wristband 3 open, and with the opened wristband 3 positioned on a charging station 5. Charging station 5 may be configured as a charging/docking station that allows data to be exchanged between charging station 5 and a computing device or an electronic storage medium. A wristband contact 7 is shown schematically at one end of a part of the wristband 3, allowing differentiation between the open and closed states of the wristband 3.

FIG. 3 also shows first and second radio antennas 9a and 9b, respectively, incorporated into the wristband 3 and used for transmitting data, thereby acquired, via wireless message transmission to a service center. As explained in greater detail below, in addition to the wristband contact 7, the antennas 9a and 9b may also serve as detectors for characterizing an operating position of the measurement instrument 1 relative to the body of the wearer or relative to the charging station 5.

Figure 5:
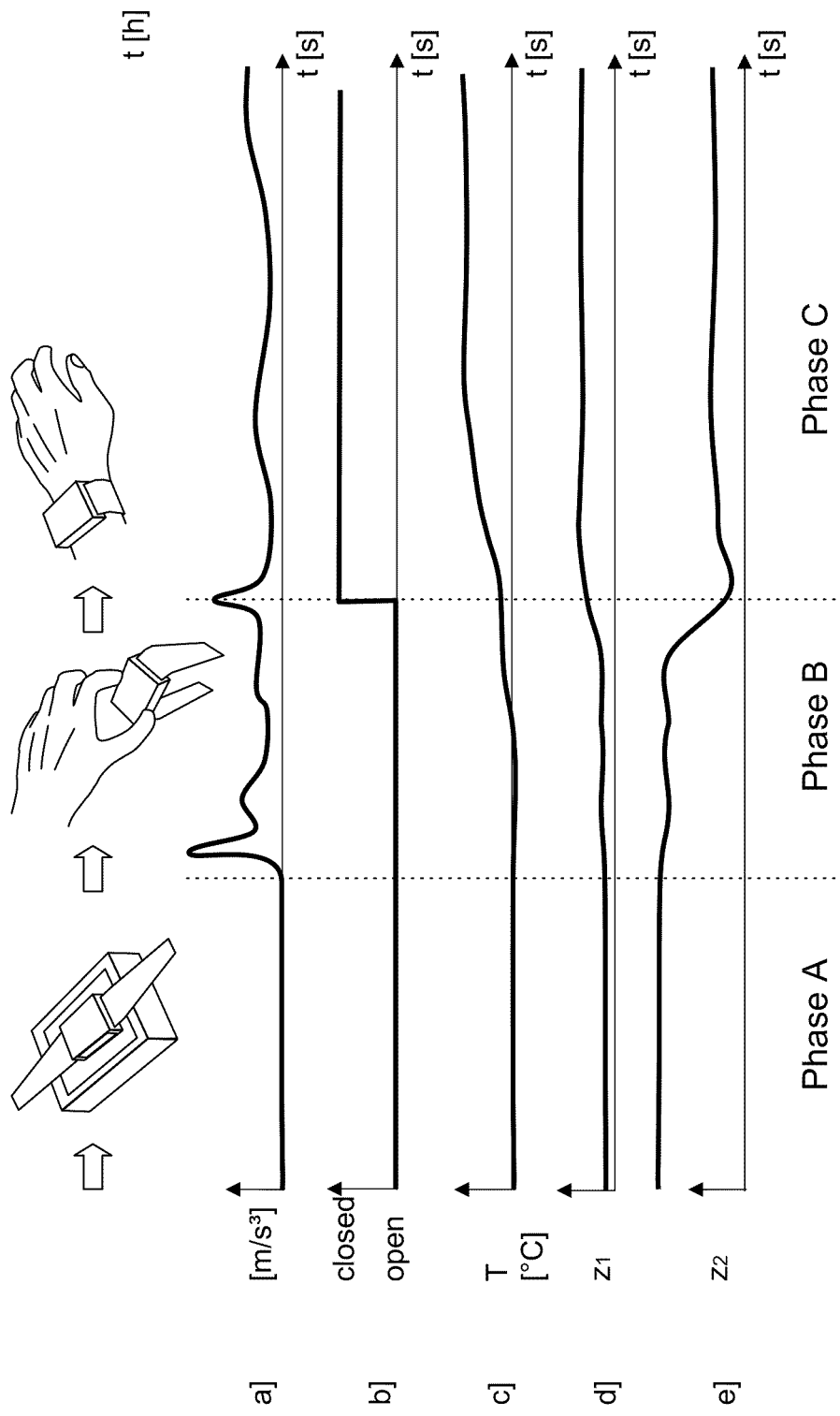
FIG. 5 is a series of plots showing changes in sensor data for detected position-dependent parameters as a function of time, for three different phases of operation of the measurement instrument: phase A—while the measurement instrument is in a charging position; phase B—while the measurement instrument is in transit from a charging position to an operating position; and phase C—while the measurement instrument is in an operating position, in contact with the subject's wrist.

FIG. 5 shows, in a synoptic diagram, time-dependent signal curves of detected position parameters that may be used for characterizing the position of the measurement instrument 1, while at rest, connected to the charging station 5 (phase A); after being removed from charging station 5 while being applied to the wearer's wrist (phase B); and in a normal operational state located on the wearer's wrist (phase C). Row a] shows the time dependence of an acceleration signal; row b] shows a binary signal derived from the wristband contact 7; row c] shows the signal of a temperature sensor integrated into the measurement instrument 1; row d] shows the real part of the impedance (simulated) from the antenna 9a; and row e] shows the real part of the impedance (simulated) from the antenna 9b (see also FIG. 8, and the respective explanation). It can be seen here that different position-dependent parameters, having different degrees of significance, provide information about the actual position of the measurement instrument and thus can be used for differentiating between predefined position states and operating states.

The list of position-dependent parameters shown in FIG. 5 is not necessarily complete. In addition, a capacitive sensor that responds to the proximity of water retained in bodily tissue may be provided to infer proximity to the body of the wearer. A charge state sensor in measurement instrument 1 may ascertain whether or not measurement instrument 1 is docked on the charging station 5, precluding being on the subject's body, or whether an optical sensor contained in the measurement instrument 1 may detect reflection through the skin. A housing section of the charging station 5 (see also FIG. 6 and the respective description below) or a similar optical sensor may respond to periodic optical features near the measurement instrument 1 and thus may acquire a pulse signal, indicating that the measurement instrument 1 is on the subject's body. Likewise, an acoustic sensor may detect pulse sounds or other body sounds. Through suitable electrodes, impedance values near the measurement instrument 1, muscle action potentials, or cardiac action potentials may be detected, thus indicating proximity to body tissue.

Figure 6:
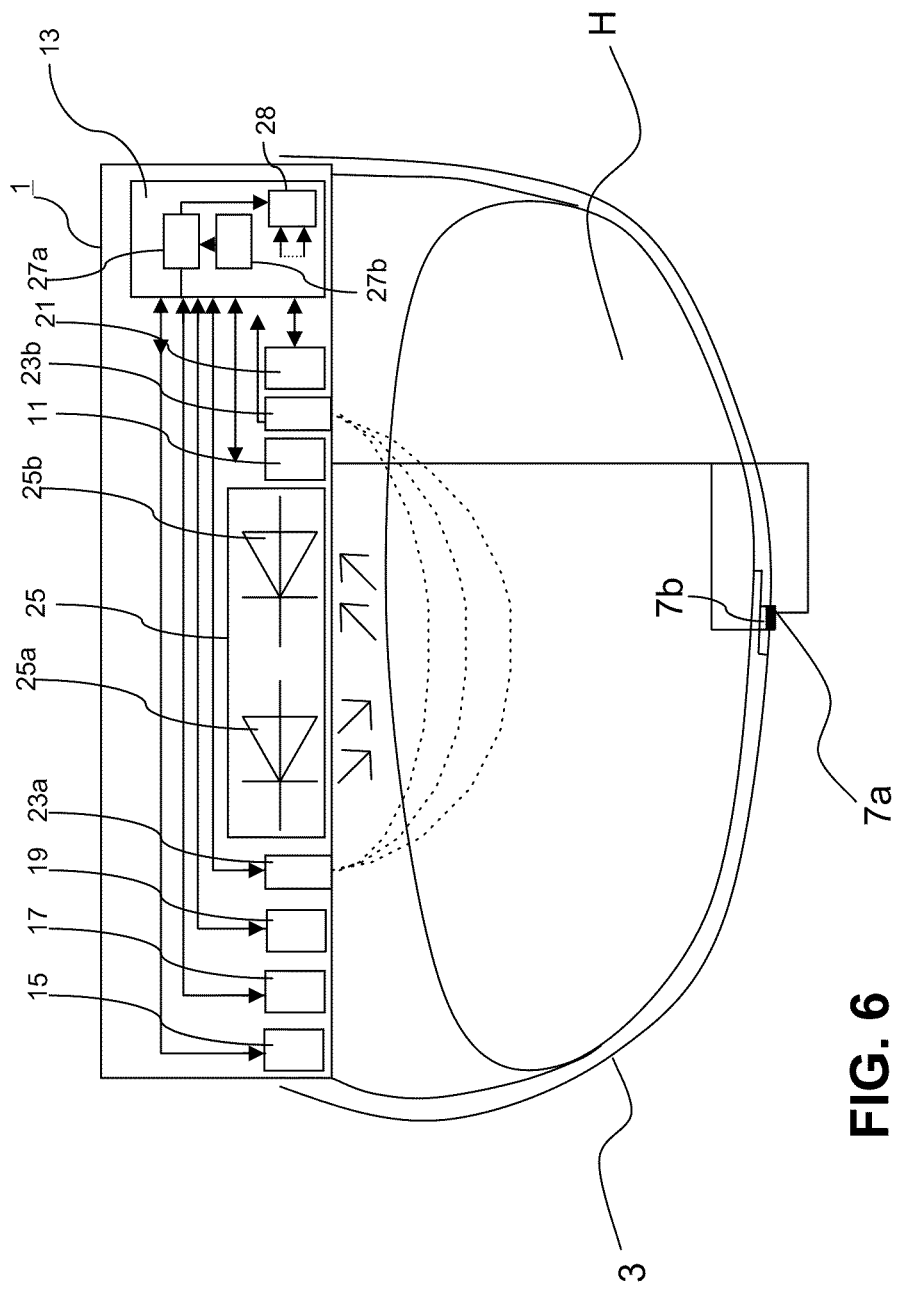
FIG. 6 is a combined cross-sectional view and schematic diagram showing a wearable measurement instrument comprising an operating-position-determining unit, and a detector, implemented as a plurality of sensors, for detecting position-dependent parameters such as those shown in FIG. 5, while in an operational position attached to a subject's wrist.

FIG. 6 shows schematically in the manner of a block diagram a design of an embodiment of the wearable measurement instrument 1 according to FIGS. 1-4, in cross section, and in greater detail. FIG. 6 shows a two-part design of the wristband contact consisting of a first contact part 7a and a second contact part 7b in combination with inputs of a contact state sensor 11, which is in turn connected to an input of an operating-position-determining unit 13. In addition to contact state sensor 11 for detection of a position-dependent parameter, additional sensors providing parameter detection may include an acceleration sensor 15, a temperature sensor 17, a capacitive sensor 19 and an acoustic sensor 21, each of which is also connected to inputs of the operating-position-determining unit 13.

In addition, a first electrode 23a and a second electrode 23b are arranged on a bottom surface of the wearable measurement instrument 1, by means of which it is possible to detect and measure ambient capacitance on the underside of the measurement instrument 1 and thus to perform a capacitive determination of the presence or absence of [water-retaining] body tissue in the vicinity of the electrodes. The electrodes 23a and 23b are also connected to the operating-position-determining unit 13 to supply an acquired capacitance signal. Electrodes 23a and 23b may provide a capacitance or impedance measurement. Alternatively, different electrode pairs (optionally, the two parts of wristband 3) may be provided for measuring capacitance and impedance. Through an unambiguously differentiable impedance spectrum, as well as through significant changes in capacitance in comparison with air or a section of the charging station 5, the proximity of living tissue may be detected, and it may be deduced that measurement instrument 1 is located on the wearer's body.

Finally, the measurement instrument 1 includes an optical sensor system 25 having an optical transmission unit 25a and an optical receiving unit 25b, which is designed for transmitting light from the underside of the measurement instrument 1 and for receiving and analyzing reflections. The receiving unit 25b is embodied, in a manner known to a person of skill in the art, such that it can differentiate reflections originating from neighboring body tissue and reflections originating from plastic material of the charging station 5, the wristband 3, or the like. The optical sensor system 25 may also be designed to implement an especially reliable method for determining the operating position of the measurement instrument 1, namely by detecting the pulse of the wearer. The presence of a pulse constitutes an unambiguous sign that the measurement instrument 1 is in direct contact with the body of the wearer. Acoustic sensor 21 may also be adapted specifically to the detection of the wearer's pulse.

In the operating-position-determining unit 13, which is preferably equipped with a processor and random access memory (RAM) as well as a program memory, there may be combined processing of the signals of the various position-variable sensors in order to derive a conclusion about the current operating position of the measurement instrument 1 in the most reliable possible manner. This processing includes threshold value discrimination on the basis of threshold values determined in advance for at least some of the position parameters. This is shown in FIG. 6 by the output signal of the temperature sensor 17, which constitutes a first input of a comparator 27a which is connected by a second input to a programmable comparative value memory 27b and whose output leads to a combination evaluation block 28, where the preprocessing data of the various position parameters are combined to derive the overall result.

Figure 7:
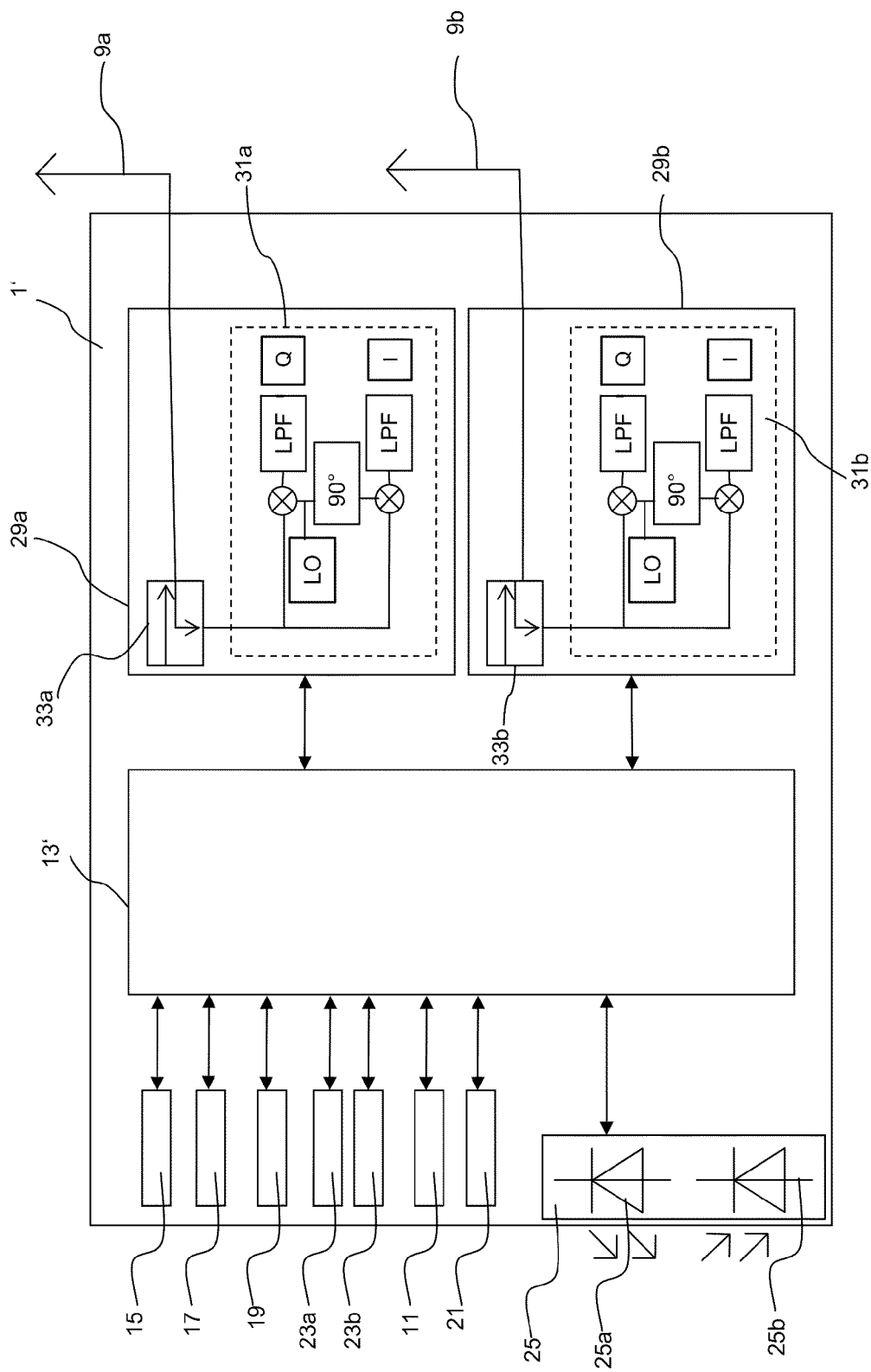
FIG. 7 is functional block diagram of a preferred embodiment of a wearable measurement instrument.

FIG. 7 shows a measurement instrument 1' which is a modified embodiment of the measurement instrument 1, including, in addition to the parameter detector, two modules that allow an additional signal to be extracted from the emission and tuning behavior of two antennas 9a and 9b (as shown in FIGS. 3 and 4). HF transmission/receiving units 29a and 29b are connected to each of the two antennas 9a and 9b, respectively. The antennas and the respective transmission/receiving units are provided for various transmission/reception areas and standards, e.g., the antenna 9a and the transmission/receiving unit 27a are provided for a mobile radio transmission according to the GSM standard or the GPRS standard, and the antenna 9b and the transmission/receiving unit 29b are provided for a short-range data transmission in the MICS band. In the design of both transmission/receiving units (indicated schematically in FIG. 7), specific position-variable-detectors are provided and both transmission/receiving units 29a and 29b are connected to inputs of the operating-position-determining unit 13 for transfer of the position variable signals detected.

With the help of a remote implementation of transmission/receiving unit 29a, measured information may be transmitted to an external service center, where it may be used for evaluation of the sensor information. With the help of a short-distance implementation of transmission/receiving unit 29b, measured information may be transmitted to an implant that cooperates with the wearable measurement instrument 1'. The quality of the external measured value is likewise assessed with this information in the implant and a decision is made about whether or not the measured value is allowed to enter into a decision that will affect treatment.

Within the transmission/receiving units 29a, 29b, the antenna impedance and the power reflected to the antennas 9a, 9b are measured in amplitude and phase via an IQ demodulator 31a and 31b, each being connected via directional coupler 33a and 33b for detection of the reflected power. The reflected power signal is converted directly to the baseband using IQ demodulators 31a and 31b located in the receiver. The resulting in-phase signal (I) and quadrature signal (Q) form a complex vector IQ. The information is contained in the phase position between the I and Q components and the length of the phasor. The two baseband signals can be detected by a two-channel analog-to-digital converter (ADC). The evaluation may be performed by a threshold value decision unit, for example. The measurement may be performed at a single frequency or for greater reliability, over a frequency range. The measurement is performed on at least one of the existing transmitter and antenna subsystems (9a and 29a, or 9b and 29b).

Figure 8B:
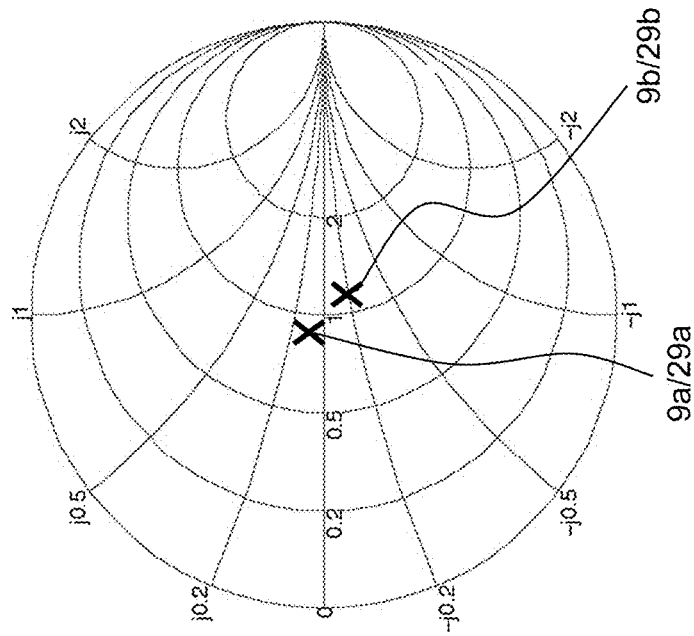
FIGS. 8A and 8B are Smith diagrams that illustrate reflected power values associated with an alternative embodiment of a wearable measurement instrument.
Figure 8A:
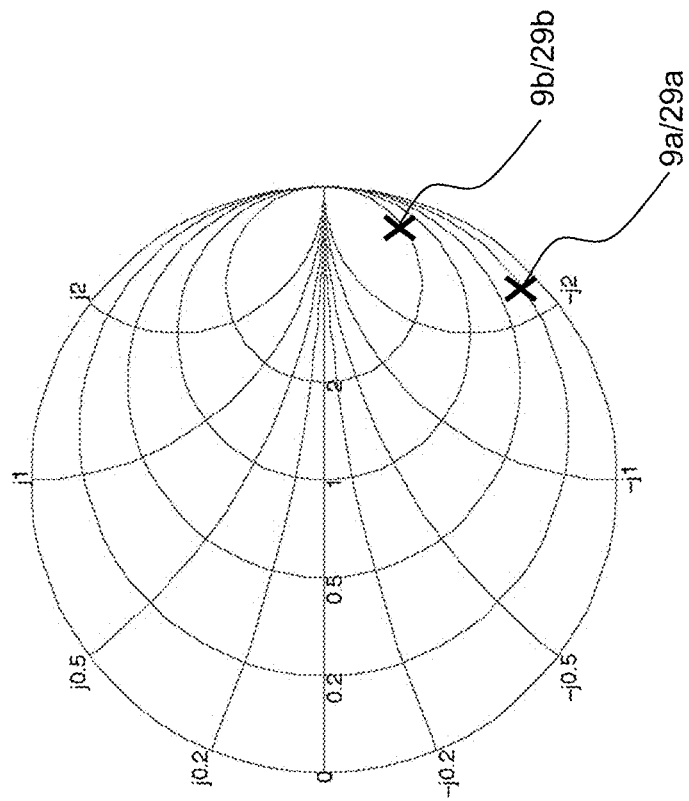

Two Smith diagrams shown in FIGS. 8A and 8B serve to illustrate IQ signals of the reflected power measured over a frequency range of 300 to 1000 MHz. FIG. 8A represents reflected power according to amplitude and phase in the case when it measurement instrument 1' is not being worn, and FIG. 8B represents the reflected power when measurement instrument 1' is being worn. The entire measurement range is preferably not surveyed continuously but instead only one frequency is surveyed at a time. In FIGS. 8A and 8B, two frequencies are marked at approx. 400 MHz (measured over antenna 9b/29b) and 800 MHz (measured over antenna 9a/29b), for example. Analysis of the Smith diagrams is known to a person of skill in the art, but to facilitate an understanding, it is emphasized that with optimal adjustment of an antenna, the imaginary part of the IQ signal is about zero. The antennas are usually embodied in such a way that this is the case in the desired operating state, e.g., when measurement instrument 1' is worn on the wrist.

The differences between both cases represented here, in particular the much better adaptation of the antenna impedance for the case in which the measurement instrument is being worn in comparison with the device being in the charging station are clearly discernible. The reason for the change is the difference in the dielectric constants of the subject's arm and the dielectric constant of the charging station, which influences the effective wavelength, and thus the antenna impedance.

The IQ measurement is performed as needed, preferably before recording a vital parameter. Each measurement yields an IQ dataset over the desired frequency bandwidth. Thus, on the basis of one IQ measurement, the device can assess whether it is located on the subject's arm.

If the actual component at up to approx. 800 MHz (FIG. 5 *d*]), is much smaller than at 400 MHz (FIG. 5 *e*]), then the antenna impedance parameter reveals that the device is not on the subject's wrist or even near the subject's body. If the real component is approximately the same size at both frequencies, it indicates that the device is being worn on the subject's wrist.

Figure 9:
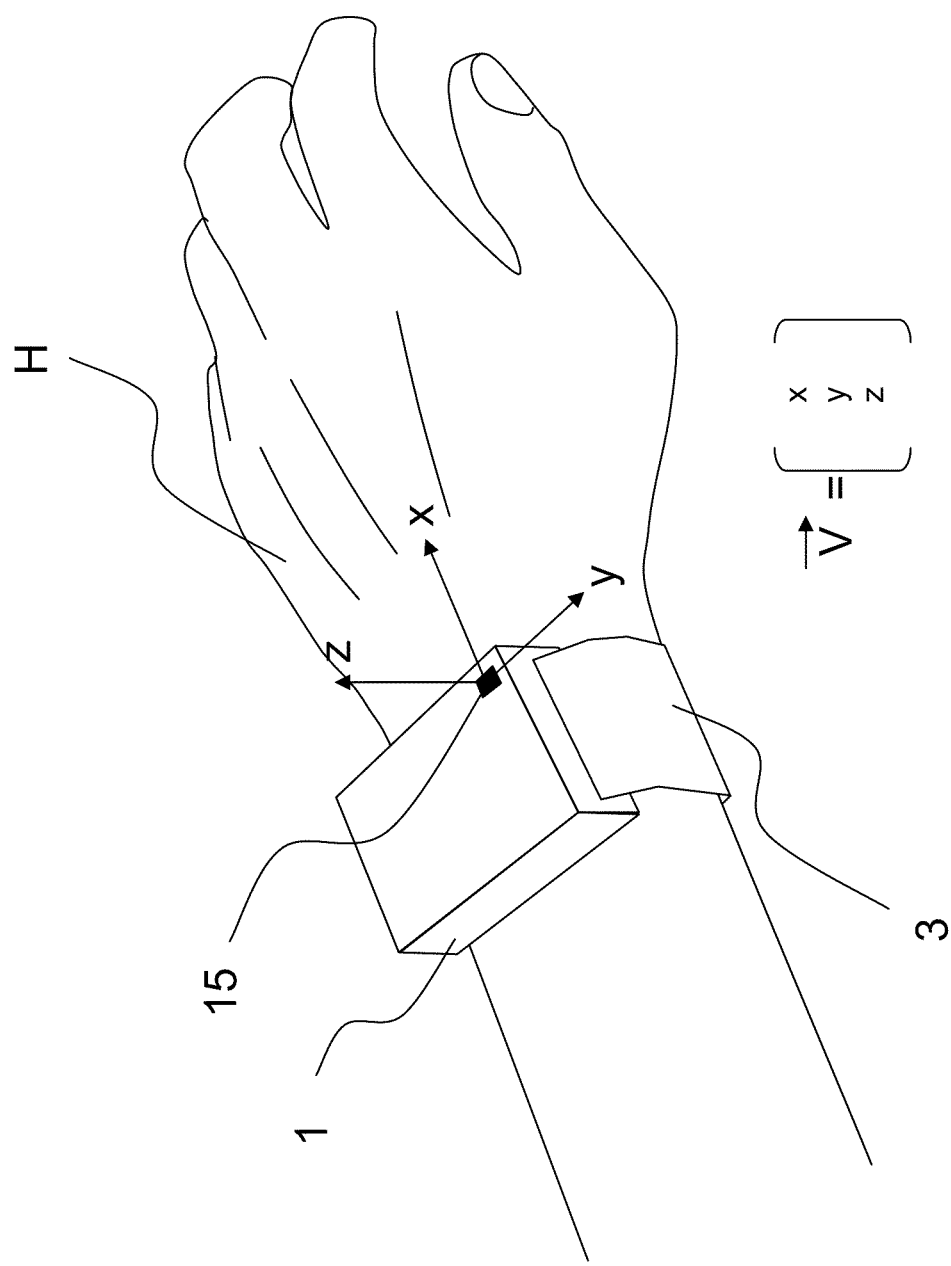
FIG. 9 is a pictorial perspective view of an exemplary wearable measurement instrument, along with coordinate axes showing directional components of a measured acceleration vector V.

Like FIG. 1, FIG. 9 shows in a schematic diagram a wearable measurement instrument 1, which is attached to the wrist of a wearer's hand H by means of a wristband 3 having an acceleration sensor 15. The acceleration sensor 15 is capable of detecting acceleration directed along any one of three orthogonal measurement axes and outputting the acceleration in the form of an acceleration vector V(x,y,z) having vector components x, y, and z. In an exemplary embodiment, the acceleration sensor 15 consists of three individual sensors for the three axes arranged orthogonally, each sensor detecting acceleration in a direction along the respective measurement axis. The acceleration vector V(x,y,z) thus represents signals detected by the three individual sensors for the three axes.

As mentioned above, the operating-position-determining unit 13 (FIG. 6), or 13' (FIG. 7), has available the input signals of the connected position variable sensors and determines the probability of the measurement instrument 1 being worn on the subject's arm. This information is further made available to an internal sensor evaluation unit, which is optionally present in one or more transmission units.

According to a simple approach, a binary marker may be generated from the measured values, indicating whether or not the measurement instrument is being worn as intended, i.e.,

| watch_worn = 0 | watch is not worn |
| watch_worn = 1 | watch is being worn. |

According to a more complex approach, an index may be generated whose value indicates the probability of the measuring instrument 1 (abbreviated here as a "watch") being worn as intended. Thus the probability index yields an indicator of the accuracy of this conclusion. For example,

| probability_watch_is_worn = 0.01 | watch is not being worn |
| probability_watch_is_worn = 0.87 | watch is being worn. |

In addition, an index may also be used to conclude about how closely the measuring instrument 1 is in contact with the wrist. This allows conclusions to be made about the dynamic behavior of measuring instrument 1 (e.g., via the acceleration measurement) as well as the determination of the quality and validity of a measurement.

In another application, signals detected by the acceleration sensor 15 may be used to ascertain whether the measurement instrument 1 is being worn on the right arm or the left arm.

In FIG. 9, measurement directions of the components of acceleration vector V along three orthogonal measurement axes associated with acceleration sensor 15 are shown as an example along with a vector representation of the measurement results. If the magnitude $Sqrt(x^2+y^2+z^2)$ of the measured acceleration vector V(x,y,z) is approximately 1, then the measurement system is at rest. Then an analysis of the acceleration vector components x, y, and z, measured in the three spatial directions may provide information about whether the measurement instrument 1 is being worn on the subject's right or left arm. The direction of the prevailing gravitational acceleration may be used as a reference here.

Figure 10:
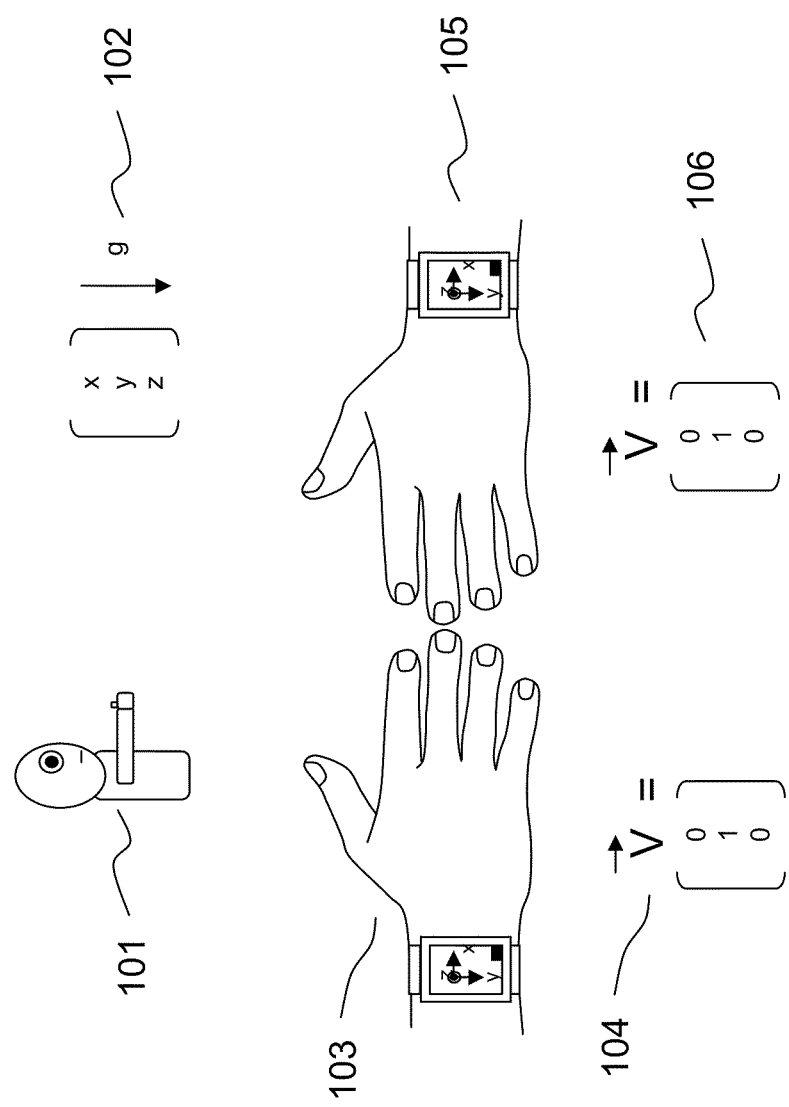
FIG. 10 is a set of pictorial views and corresponding measured acceleration vectors associated with a first exemplary orientation of a wearable measurement instrument when the subject's arms are extended and the hands are vertical.
Figure 11:
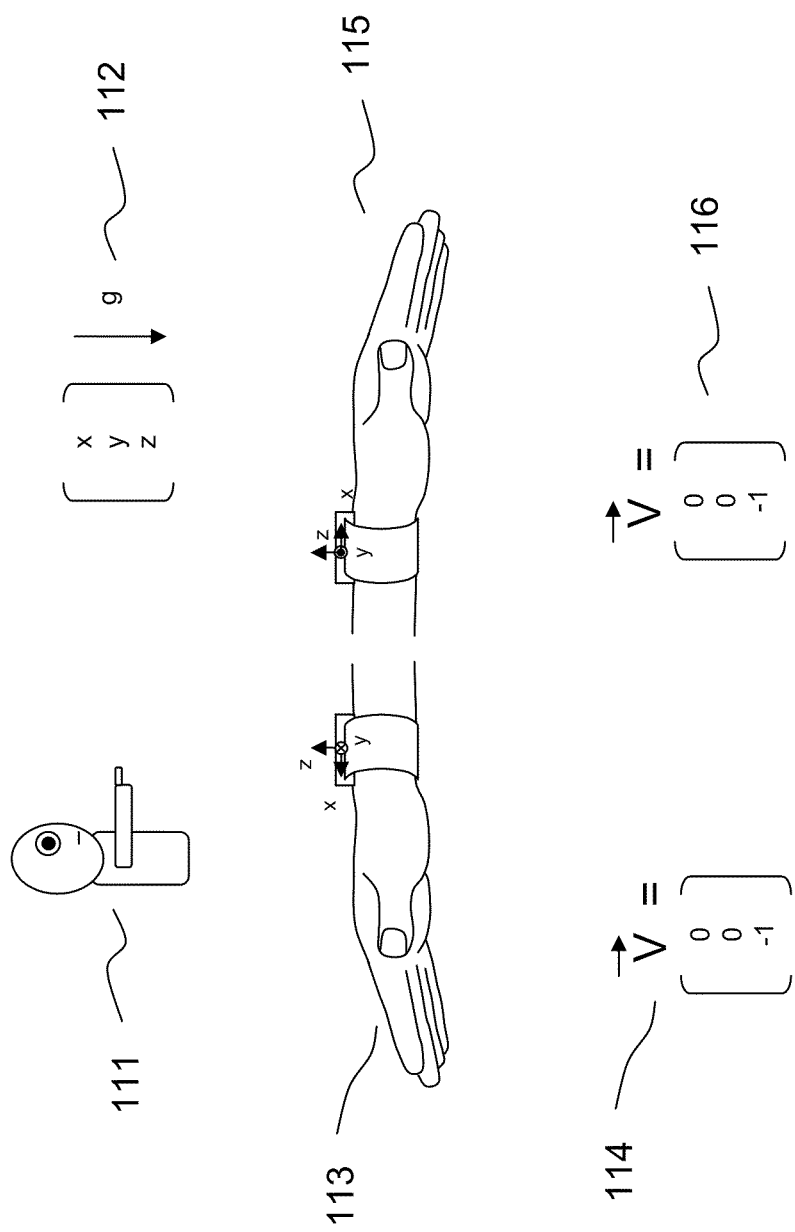
FIG. 11 is a set of pictorial views and corresponding acceleration vectors associated with a second exemplary orientation of a wearable measurement instrument when the subject's arms are extended and the hands are horizontal.
Figure 12:
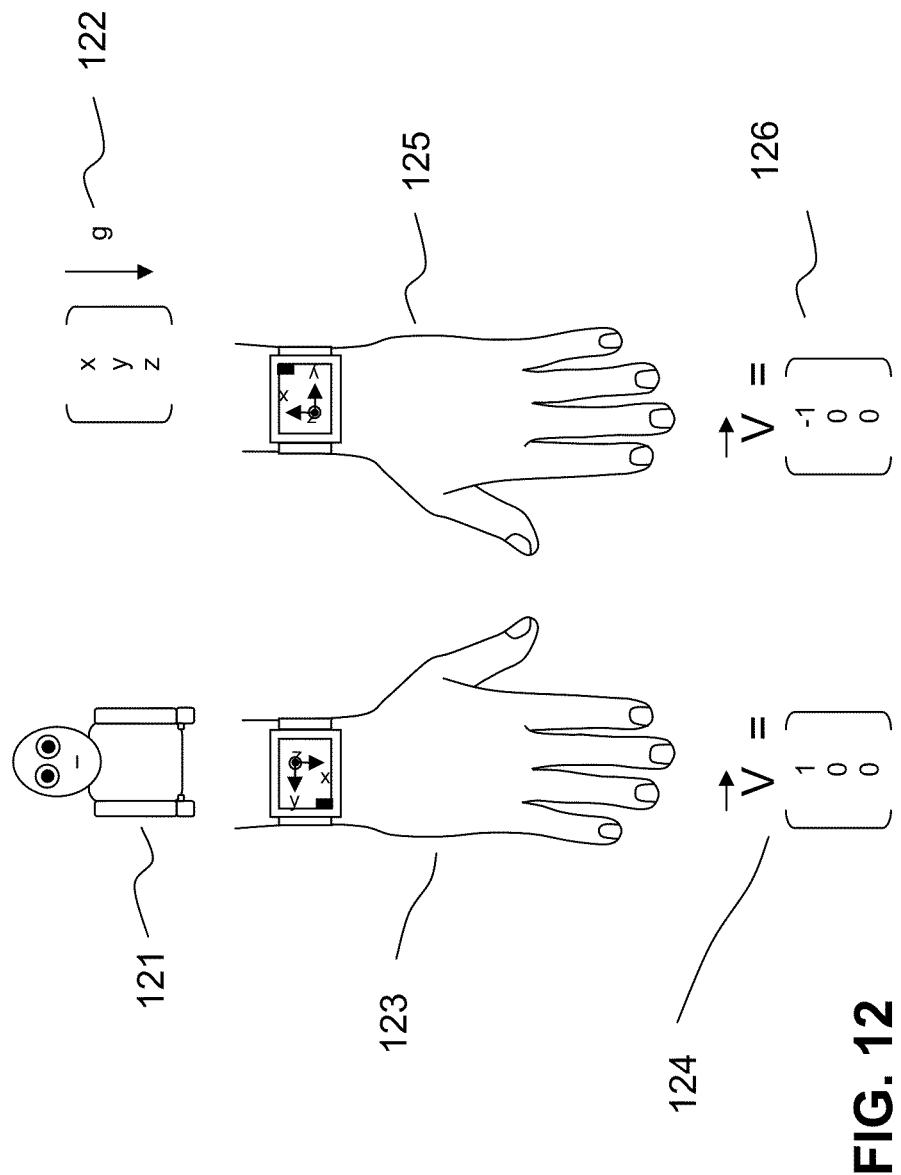
FIG. 12 is a set of pictorial views and corresponding measured acceleration vectors associated with a third exemplary orientation of a wearable measurement instrument when the subject's arms are hanging down.

FIGS. 10, 11 and 12 show various positions of the measurement instrument 1 and the measured values of V(x,y,z) detected by acceleration sensor 15 along the coordinate axes, normalized to the gravitational acceleration vector g as an example. FIG. 10 shows a) a first position of the measurement instrument 1 when the subject's arms are extended in a forward position 101, and in which the subject's hand is oriented vertically, generally perpendicular to the earth's surface; b) the direction of the earth's gravitational field g 102; c) the alignment of the measurement instrument 1 worn on the subject's right arm 103; d) the alignment of the measurement instrument 1 worn on the subject's left arm 105; and e) the resulting value of the vector V(x.y,z) 104 for a measurement instrument 1 worn on the right arm 103; and f) the resulting value of the vector V(x,y,z) 106 for a measurement instrument 1 worn on the left arm.

FIG. 11 shows a) a second position of the measurement instrument 1 when the subject's arms are extended in a forward position 111, and in which the subject's hand is oriented horizontally, generally parallel to the earth's surface; b), the direction of the earth's gravitational field g 112; c) the alignment of the measurement instrument 1 worn on the subject's right arm 113; d) the alignment of the measurement instrument 1 worn on the subject's left arm 115; e) resulting values of the vector V(x,y,z) 114 for a measurement instrument 1 worn on the right arm; and f) resulting values of the vector V(x,y,z) 116 for a measurement instrument 1 worn on the left arm.

FIG. 12 shows a) a third position of the measurement instrument 1 for which the subject's arms are hanging down 121; b) the alignment of the earth's gravitational field 122; c)

the alignment of the measurement instrument 1 worn on the subject's right arm 123; d) the alignment of the measurement instrument 1 worn on the subject's left arm 125; e) resulting values of the vector V(x,y,z) 124 for a measurement instrument 1 worn on the right arm; and f) resulting values of the vector V(x,y,z) 126 for a measurement instrument 1 worn on the left arm. When the measurement instrument 1 is the positions illustrated in FIGS. 10 and 11, differentiation of whether the measurement instrument 1 is being worn on the right or left arm is not possible, but it is possible for the position shown in FIG. 12. If the measurement instrument 1 is worn in accordance with the methods described above, then an acceleration measurement using the acceleration sensor 15 may be performed at regular intervals, e.g., every minute. The resulting vector V(x,y,z) is then analyzed. If vector V(x,y,z) is much larger or smaller than 1, then the system is determined to be "in motion" and the measurement is discarded.

If the vector V(x,y,z) is equal to or approximately 1, then it is determined that the system is at rest and the value of x is analyzed. If the value of x is close to 0, then it is impossible to state accurately whether the measurement instrument is being worn on the right arm or the left arm. If the absolute value of acceleration in a direction parallel to the x-axis is much greater than the values of acceleration along the y and z axes, then the measurement instrument 1 is approximately in one of the two positions shown in FIG. 12. If x is greater than zero, then the measurement instrument 1 is likely to be worn on the right arm. If x is less than zero, then the measurement instrument 1 is likely to be worn on the left arm. It may of course happen that the subject's arm is not hanging down, but instead is being raised. This would then result in a "side-switched" result. Therefore, one point may be issued per measurement for "probably on the left" or "probably on the right," for example. Because a subject's arm is typically hanging down more often than it is being held up, a correct result may be ascertained.

Embodiments of the invention are not limited to the examples described above, and aspects that have been emphasized here but instead may also lie in a variety of modifications which are within the scope of technical action.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A physiological measurement instrument capable of detecting and measuring values of one or more physiological measurement parameters associated with a body of a human or animal subject, the measurement instrument comprising:
   a. a detector, implemented as one or more sensors, for use in detecting values of the measurement parameters, the values indicating an operating position of the measurement instrument wherein the operating position is relative to the body, or to a certain location of the measurement instrument;
   b. an operating-position-determination unit that receives and analyzes output signals from the detector, to determine the operating position of the measurement instrument wherein the operating position is relative to the body, or to a certain location of the measurement instrument, wherein:
      (1) the operating-position-determination unit comprises a comparator that compares the detected values against a standard to determine the operating position of the measurement instrument, wherein the standard is a predetermined threshold value or a comparative parameter, and
      (2) the operating-position-determining unit produces a multi-valued output signal for differentiation of a first operating position at the body, a second operating position in a charging station, and a third operating position located away from both the first and second operating positions; and
   c. a multi-part fastener for attaching to the body of the subject, in which the fastener has contact areas that make contact with one another when the fastener is in a closed state but do not make contact with one another when the fastener is in an open state, and in which the detector determines the contact state of the fastener.

2. The measurement instrument according to claim 1, wherein the detector is capable of detecting an absolute value and a time-varying value of a position-dependent variable.

3. The measurement instrument according to claim 1, wherein the operating-position-determining unit produces an index value, which expresses a probability of the measurement instrument being in one of several predetermined operating positions.

4. The measurement instrument according to claim 1, wherein the detector has a capacitive sensor system for detection of the proximity of the measurement instrument to the body on a capacitive basis.

5. The measurement instrument according to claim 1, further comprising a radio antenna for emitting a radio signal, wherein the detector is capable of detecting a complex impedance of the antenna.

6. The measurement instrument according to claim 1, wherein the detector comprises a temperature sensor.

7. The measurement instrument according to claim 1, wherein the detector comprises an optical sensor system, located in an area of the measurement instrument that faces the body when the measurement instrument is in operation, for optical detection of either a neighboring body section or a section of a charging station.

8. The measurement instrument according to claim 1, wherein the detector further comprises either an optical sensor system, for detection of periodic physiological signals such as a pulse rate, or an acoustic sensor system for detection of periodic physiological signals such as a pulse rate or heart sounds.

9. The measurement instrument according to claim 1, wherein the detector is capable of detecting physiological electrical potentials, such as cardiac action potentials or muscle action potentials, as an indicator of proximity of the measurement instrument to a body section.

10. The measurement instrument according to claim 1, further comprising multiple detectors for detecting values of different physical parameters, wherein the operating-position-determining unit is capable of combined evaluation of output signals of the multiple detectors for supplying an output signal representing the operating position of the measurement instrument relative to the body.

11. The measurement instrument according to claim 1, further comprising multiple detectors for use in detecting values of a physical parameter in different sections of the measurement instrument, wherein the operating-position-determining unit is capable of combined analysis of output signals of the multiple detectors for supplying an output signal representing the operating position of the measurement instrument relative to the body.

12. A physiological measurement instrument capable of detecting and measuring values of one or more physiological measurement parameters associated with a body of a human or animal subject, the measurement instrument including:
  a. a detector defined by one or more sensors, the detector being configured to detect values of the measurement parameters, the values indicating an operating position of the measurement instrument wherein the operating position is relative to the body, or to a certain location of the measurement instrument;
  b. an operating-position-determination unit configured to receive output signals from the detector and determine the operating position of the measurement instrument therefrom, wherein:
    (1) the operating position is relative to the body, or to a certain location of the measurement instrument,
    (2) the operating-position-determination unit includes a comparator that compares the output signals against a standard to determine the operating position of the measurement instrument, the standard being a predetermined threshold value or a comparative parameter,
    (3) the operating-position-determining unit produces a multi-valued output signal for differentiation of a first operating position located at a certain body area, a second operating position located in a charging station, and a third operating position located away from both the first and second operating positions, wherein the certain body area is the right half of the body, the left half of the body, or one of the extremities; and
  c. a multi-part fastener configured to attach to the body of the subject, wherein:
    (1) the fastener has contact areas that make contact with one another when the fastener is in a closed state but do not make contact with one another when the fastener is in an open state, and
    (2) the detector determines the contact state of the fastener.

13. A physiological measurement instrument for detecting and measuring values of physiological parameters associated with a human or animal body, the measurement instrument including:
  a. a detector having one or more sensors configured to measure values of the physiological parameters; and
  b. an operating-position-determination unit configured to:
    (1) compare the measured values against one or more standards, and
    (2) determine from the comparison at least one of:
      (a) the location of the measurement instrument relative to at least one operating position, and
      (b) the location of the measurement instrument upon at least one of the operating positions,
      wherein one of the operating positions is the body;
    (3) generate a multi-valued output signal, wherein different values of the output signal define the measurement instrument's location at the following operating positions:
      (a) on the body, and
      (b) at a measurement instrument charging station, and
      (c) away from both the body and the measurement instrument charging station; and
  c. further including an antenna configured to emit a radio signal, wherein the detector is configured to measure a complex impedance of the antenna.

14. The measurement instrument of claim 13 wherein:
  a. the detector includes several different sensors configured to measure values of different physiological parameters,
  b. the operating-position-determination unit is configured to determine the location of the measurement instrument relative to the body.

15. The measurement instrument of claim 13 wherein the detector includes a capacitive sensor configured to generate an output signal indicative of the proximity of the measurement instrument.

16. The measurement instrument of claim 13 wherein the detector includes a temperature sensor.

17. The measurement instrument of claim 13 wherein the detector includes at least one of:
  a. an optical sensor system, and
  b. an acoustic sensor system, configured to detect periodic physiological parameters.

18. The measurement instrument of claim 13 wherein the detector includes an electrical action potential sensor configured to detect physiological electrical potentials.

19. A physiological measurement instrument for detecting and measuring values of physiological parameters associated with a human or animal body, the measurement instrument including:
  a. a detector having one or more sensors configured to measure values of the physiological parameters; and
  b. an operating-position-determination unit configured to:
    (1) compare the measured values against one or more standards, and
    (2) determine from the comparison at least one of:
      (a) the location of the measurement instrument relative to at least one operating position, and
      (b) the location of the measurement instrument upon at least one of the operating positions,
      wherein one of the operating positions is the body, and
  c. generate an output signal defining a probability that the measurement instrument is in one of several predetermined operating positions.

20. The measurement instrument of claim 19 wherein:
  a. the measurement instrument further includes an antenna thereon configured to emit a radio signal, and
  b. the detector is configured to measure a complex impedance of the antenna.

21. The measurement instrument of claim 19 wherein the measurement device further includes a fastener configured to:
  a. attach the measurement instrument adjacent to the body, and
  b. generate an output signal indicative of attachment.

22. The measurement instrument of claim 19 wherein the output signal defines:
  a. a probability that the measurement instrument is at a first operating position located at the body, and
  b. a probability that the measurement instrument is a second operating position located away from the body.

23. The measurement instrument of claim 19 wherein the output signal defines:
  a. a probability that the measurement instrument is at a first operating position located at the body;
  b. a probability that the measurement instrument is a second operating position in a charging station; and
  c. a probability that the measurement instrument is a third operating position located away from both the first and second operating positions.

24. The measurement instrument of claim 19 wherein the detector includes an optical sensor system situated on the measurement instrument to face the body when the measurement instrument is located on the body.

25. The measurement instrument of claim 19 wherein the detector includes at least one of:
  a. an optical sensor system, and
  b. an acoustic sensor system,
  configured to detect periodic physiological parameters.

26. A physiological measurement instrument for detecting and measuring values of physiological parameters associated with a human or animal body, the measurement instrument including:
- a. a detector having one or more sensors configured to measure values of the physiological parameters, the sensors including an optical sensor system situated on an area of the measurement instrument that faces the body when the measurement instrument is located thereon, and
- b. an operating-position-determination unit configured to:
  - (1) compare the measured values against one or more standards, and
  - (2) determine from the comparison at least one of:
    - (a) the location of the measurement instrument relative to at least one operating position, and
    - (b) the location of the measurement instrument upon at least one of the operating positions,
  - wherein one of the operating positions is the body;
- the measurement instrument being configured to generate a multi-valued output signal, wherein different values of the output signal define the measurement instrument's location at the following operating positions:
  - (1) on the body, and
  - (2) at a measurement instrument charging station, and
  - (3) away from both the body and the measurement instrument charging station.

27. The measurement instrument of claim 26 wherein:
- a. the measurement instrument further includes an antenna thereon configured to emit a radio signal, and
- b. the detector is configured to measure a complex impedance of the antenna.

28. The measurement instrument of claim 26 wherein the measurement device further includes a fastener configured to:
- a. attach the measurement instrument adjacent to the body, and
- b. generate an output signal indicative of attachment.

* * * * *

UNITED STATES PATENT AND TRADEMARK OFFICE
CERTIFICATE OF CORRECTION

PATENT NO.        : 8,854,060 B2
APPLICATION NO.   : 12/917183
DATED             : October 7, 2014
INVENTOR(S)       : Diebold et al.

Page 1 of 1

It is certified that error appears in the above-identified patent and that said Letters Patent is hereby corrected as shown below:

CORRECTION TO ITEM (73) ASSIGNEE NAME ON TITLE PAGE:

Assignee's correct name is BIOTRONIK CRM Patent AG, not BIOTRONIK CRIM Patent AG.

Signed and Sealed this
Sixth Day of January, 2015

Michelle K. Lee
*Deputy Director of the United States Patent and Trademark Office*